(12) United States Patent
Makriyannis et al.

(10) Patent No.: US 7,276,613 B1
(45) Date of Patent: *Oct. 2, 2007

(54) RETRO-ANANDAMIDES, HIGH AFFINITY AND STABILITY CANNABINOID RECEPTOR LIGANDS

(75) Inventors: Alexandros Makriyannis, Watertown, MA (US); Qian Liu, Storrs, CT (US); Andreas Goutopoulos, Boston, MA (US)

(73) Assignee: University of Connecticut, Farmington, CT (US)

( * ) Notice: Subject to any disclaimer, the term of this patent is extended or adjusted under 35 U.S.C. 154(b) by 146 days.

This patent is subject to a terminal disclaimer.

(21) Appl. No.: 10/110,862

(22) PCT Filed: Oct. 18, 2000

(86) PCT No.: PCT/US00/41248

§ 371 (c)(1),
(2), (4) Date: Oct. 21, 2002

(87) PCT Pub. No.: WO01/28498

PCT Pub. Date: Apr. 26, 2001

Related U.S. Application Data

(63) Continuation-in-part of application No. 09/600,786, filed as application No. PCT/US99/28136 on Nov. 29, 1999, now Pat. No. 7,161,016.

(60) Provisional application No. 60/160,033, filed on Oct. 18, 1999, provisional application No. 60/109,615, filed on Nov. 24, 1998.

(51) Int. Cl.
C07C 231/00 (2006.01)
C07C 233/00 (2006.01)
C07D 265/30 (2006.01)

(52) U.S. Cl. .................... 554/35; 554/67; 554/106; 564/192

(58) Field of Classification Search ................ 514/162, 514/613, 625, 627, 298, 309; 564/204, 192; 544/66, 106; 560/249; 554/35, 67
See application file for complete search history.

(56) References Cited

U.S. PATENT DOCUMENTS

| | | | |
|---|---|---|---|
| 3,041,343 A | 6/1962 | Jucker et al |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |

(Continued)

FOREIGN PATENT DOCUMENTS

EP 0276732 8/1988

(Continued)

OTHER PUBLICATIONS

Berglund et al, Prostanglandins, Leukotrienes and Essential Fatty Acids (1998) 59(2) pp. 11-118, as described in CA 130:151.*

(Continued)

*Primary Examiner*—Taylor Victor Oh
(74) *Attorney, Agent, or Firm*—Alix, Yale & Ristas, LLP

(57) ABSTRACT

Novel retro-anandamides are presented which have high affinities for the cannabinoid CB1 and/or CB2 receptor sites. Further, most of the analogs exhibit greater metabolic stability than arachidonylethanolamide. The improved receptor affinity and selectivity and/or greater metabolic stability make these analogs therapeutically useful as medications in individuals and animals for treatment of pain, glaucoma, epilepsy, nausea associated with chemotherapy, as well as suppression of the immune system, enhancement of appetite and in treatment of certain mental disorders.

22 Claims, No Drawings

U.S. PATENT DOCUMENTS

| | | | |
|---|---|---|---|
| 5,053,548 A | 10/1991 | Tanaka et al. | |
| 5,068,234 A | 11/1991 | D'Ambra et al. | |
| 5,147,876 A | 9/1992 | Mizuchi et al. | |
| 5,223,510 A | 6/1993 | Gubin et al. | |
| 5,284,867 A | 2/1994 | Kloog | |
| 5,324,737 A | 6/1994 | D'Ambra et al. | |
| 5,434,295 A | 7/1995 | Mechoulam et al. | |
| 5,440,052 A | 8/1995 | Makriyannis et al. | |
| 5,462,960 A | 10/1995 | Barth et al. | |
| 5,489,580 A | 2/1996 | Makriyannis et al. | |
| 5,521,215 A | 5/1996 | Mechoulam | |
| 5,532,237 A | 7/1996 | Gallant et al. | |
| 5,538,993 A | 7/1996 | Mechoulam | |
| 5,576,436 A | 11/1996 | McCabe et al. | |
| 5,605,906 A | 2/1997 | Lau | |
| 5,607,933 A | 3/1997 | D'Ambra et al. | |
| 5,618,955 A * | 4/1997 | Mechoulam et al. | 554/66 |
| 5,624,941 A | 4/1997 | Barth et al. | |
| 5,631,297 A | 5/1997 | Pate et al. | |
| 5,635,530 A | 6/1997 | Mechoulam | |
| 5,688,825 A * | 11/1997 | Makriyannis et al. | 514/423 |
| 5,744,459 A | 4/1998 | Makriyannis et al. | |
| 5,747,524 A | 5/1998 | Cullinan et al. | |
| 5,804,601 A | 9/1998 | Kato et al. | |
| 5,817,651 A | 10/1998 | D'Ambra et al. | |
| 5,872,148 A | 2/1999 | Makriyannis et al. | |
| 5,874,459 A * | 2/1999 | Makriyannis et al. | 514/425 |
| 5,925,628 A | 7/1999 | Lee et al. | |
| 5,925,768 A | 7/1999 | Barth et al. | |
| 5,932,610 A | 8/1999 | Shohami et al. | |
| 5,939,429 A | 8/1999 | Kunos et al. | |
| 5,948,777 A | 9/1999 | Bender et al. | |
| 6,013,648 A | 1/2000 | Rinaldi et al. | |
| 6,028,084 A | 2/2000 | Barth et al. | |
| 6,096,740 A | 8/2000 | Mechoulam | |
| 6,127,399 A | 10/2000 | Yuan | |
| 6,166,066 A | 12/2000 | Makriyannis et al. | |
| 6,284,788 B1 | 9/2001 | Mittendorf et al. | |
| 6,391,909 B1 | 5/2002 | Makriyannis et al. | |
| 6,579,900 B2 | 6/2003 | Makriyannis et al. | |
| 6,610,737 B1 | 8/2003 | Garzon et al. | |
| 6,864,291 B1 | 3/2005 | Fride et al. | |
| 2002/0119972 A1 | 8/2002 | Leftheris et al. | |
| 2002/0173528 A1 | 11/2002 | Fride et al. | |
| 2003/0120094 A1 | 6/2003 | Makriyannis et al. | |
| 2004/0077649 A1 | 4/2004 | Makriyannis et al | |
| 2004/0077851 A1 | 4/2004 | Makriyannis et al | |
| 2004/0087590 A1 | 5/2004 | Makriyannis et al | |
| 2005/0020679 A1 | 1/2005 | Makriyannis et al. | |

FOREIGN PATENT DOCUMENTS

| | | |
|---|---|---|
| EP | 0444451 | 9/1991 |
| EP | 0471609 | 6/1993 |
| EP | 0576357 | 12/1993 |
| EP | 0737671 A | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1990 |
| WO | WO 94/12466 | 6/1994 |
| WO | WO 97/00860 | 1/1997 |
| WO | WO 97/21682 | 6/1997 |
| WO | WO 97/45407 | 12/1997 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

Berglund et al, Prostanglandins, Leukotrienes and Essential Fatty Acids (1998) 59(2) pp. 11-118.*

Berglund et al, Structural requirement for arachidonylethanolamide interaction with CB1 and CB2, 1998, 59(2), p. 111-118.*

U.S. Appl. No. 09/600,786, Makriyannis et al (US national phase of WO 00/32200 included below).

U.S. Appl. No. 09/328,742, Makriyannis et al.

Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12): 1889-1893; 1994, CODEN: JMCMAR; ISSN: 0022-2623; XP002040932.

Barnett-Norris et al; "exploration of biologically relevant conformations of anandamid, . . . "; J. Med. Chem.; vol. 41; 4861-4872; 1998.

Beltramo M. Stella N., Calignano A., Lin S. Y., Makriyannis A., Piomelli D; "Functional Role of High-Affinity Anandamide Transport, as Revealed by Selective Inhibition"; Science; vol. 277; 1094-1097; 1997.

Beltramo M., Stella N., Calignano A., Lin S. Y., Makriyannis A., Piomelli D; "Identification and Functional Role of High Affinity Anandamide Transport"; The Neurosciences Institute.

Berglund et al; "prostanglandins, leukotrienes ands essential fatty acids" 59(2): 111-118; (1998) as described in CA130:151.

Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.

Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.

Cherest M., Lusinchi X.; "A novel electrophilic N-amidation via electron deficient complexes: action of ferric chloiride on N-acetyloxyamides"; Tetrahedron Letters; 30(6); 715-718; 1989.

*** Compton D.R. et al; J. Pharmacol. Exp. Ther.; 260; 201-209; 1992.

*** D'Amour F.E., Smith D.L.; J. Pharmacol. Exp. Ther.; 72; 74-79; 1941.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

Desarnd F., Cadas H., Piomelli D.; "Anadamide amidohydrolase activity in rat brain microsomes"; J. Biol. Chem.; 270; 6030-6035; (1995).

*** Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9: ISSN:0006-291X; XP002040933.

Deutsch D.G., Chin S.A.; "Enzymatic synthesis and degradation of anandamide, a cannabinoid receptor agonist"; Biochemical Pharmacology; 46(5); 791-796; 1993.

Fride & Mechoulam; "pharmacological activity of the cannabinoid receptor agonist; . . . "; european journal of pharmacology, vol. 231; 313-314; 1993 Abstract only.

Horrevoets A.J.G et al; "Inactivation of *Escherichia coli* outer membrane phospholipase A by the affinity label hexadecanesulfonyl fluoride"; Eur. J. Biochem.; 198; 247-253; 1991.
*** Howlett et al; "Structural requirements for arachidonyletanolamide interaction with CB1 and CB2 cannabinoid receptors; pharmacology of the carbonyl and ethanolamide groups"; Prost. Leuk. and Essen. Fatty Acids; 59(2); 1998.
Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.
*** Khanolkar A., Abadji V., Lin S., Hill W., Taha g., Abouzid K., Meng Z., Fan P., Makriyannis A.; "Head group analogues of arachidonylethanolamide, the endogenous cannabinoid ligand"; J. Med. Chem.; 39; 22; 4515-4519; (1996).
Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.
Lin S., Khanolkar A., Fan P., Goutopolous A., Qin C., Paphadjis D., Makriyannis A.; "Novel Analogues of arachidonylethanolamide (anandamide): affinities for the CB1 and CB2 Cannabinoid Receptors and Metabolic Stability"; J. Med. Chem.
Mackie K., Devane W.A., Hille B.; "Anandamide, an endogneous cannabinoid, inhibits calcium currents as a partial agonist in N18 neuroblastoma cells"; Mol. Pharmacol; 44; 498-0503 (1993).
*** Makriyannis et al; "Head group analogs of arachidonylethanolamide, the endogenous cannabinoid ligand"; J. Med. Chem; 39; 4515 1996.
*** Makriyannis et al; "Novel analogues of arachidonylethanolamide (anandamide): affinities for the CB1 and CB2 cannabinoid receptors and metabolic stability"; J. Med. Chem.; 41; 5353; 1998.
Neunhoeffer O., Gottschlich R.; "Acylating activity of O-acylated hydroxylamine derivatives"; Justus Liebigs Ann. Chem.; 736; 100-109; 1970; in German with English abstract.
*** Pertwee et al; Br. J. Pharmacol.; 105; 980 1992.
Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 5802-5807; (1999).
*** Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230; 341-348; (1994).
Razdan, R.K. et al; "The pharmacological activity of anandamide, a endogenous cannabinoid in mice"; Journal of Pharmacol. Exp. Ther.; 270(1); 219-227; 1994 (database CAPLUS on STN (Columbus, OH, USA) DN 121:99682.
*** Serdarevich B., Caroll K.K., "Synthesis and characterization of 1- and 2- monoglycerides of anteiso fatty acids"; J. Lipid Res.; 7; 277-284; (1966).
Smith P.B. et al; "The pharmacological activity of anandamide, a putative endogenous cannabinoid, . . . " journal of pharmacology and experimental therapeutics; vol. 270(1):219-227; 1994.
Twitchell, W. et al; "Cannabinoids inhibit N- and P/Q type calcium channels in cultured rat hippocampal neurons"; Journal of Neurophysiology; 78(1); 43-50; 1997 (database CAPLUS on STN (Columbus, OH, USA) DN 127:199945.
*** Vogel Z., Barg J., Levy R., Saya D., Heldman E., Mechouiam R.; "Anandamide, a brain endogenous compound, interacts specifically with cannabinoid receptors and inhibits adenylate cyclase"; J. Neurochem.; 61(1) 352-355; (1993).
U.S. App. No. 09/701,989, filed Jun. 9, 1999, *1* Makriyannis et al (copy not included, this is the U.S. National Phase of the Int'l Application published as WO 99/64389 enclosed herewith).
U.S. Appl. No. 10/110,865, filed Oct. 18, 2000, Makriyannis et al (copy not included, this is the U.S National Phase of the Int'l Applicaiton published as WO 01/28497 enclosed herewith).
U.S. Appl. No. 10/110830, filed Oct. 18, 2000, Makriyannis et al (copy not included, this is the U.S. National Phase of the Int'l Application published as WO 01/28329 enclosed herewith).
U.S. Appl. No. 10/110,812, filed Oct. 18, 2000, Makriyannis et al (copy not included, this is the U.S. National Phase of the Int'l Application published as WO 01/28498 enclosed herewith).
U.S. Appl. No. 10/111,059, filed Oct. 18, 2000, Makriyannis et al (copy not included, this is the U.S. National Phase of the Int'l Application published as WO 01/28557 enclosed herewith).
U.S. Appl. No. 10/483,482, filed Jul. 11, 2002, Makriyannis et al (copy not included, this is the U.S. National Phase of the Int'l Application published as WO 03/005960 enclosed herewith).
U.S. Appl. No. 10/493,093, filed Oct. 28, 2002, Makriyannis et al (copy not included, this is the U.S. National Phase of the Int'l Application published as WO 03/35005 enclosed herewith).
U.S. Appl. No. 10/647,544, filed Aug. 25, 2003, Makriyannis et al.
U.S. Appl. No. 10/790,498, filed Mar. 1, 2004, Makriyannis et al.
Alo, B.I.; Kandil, A.; Patil, P. A.; Sharp, M. J.; Siddiqui, M. A.; and Snieckus, v. Sequential Directed Ortho Metalation-Boronic Acid Cross-Coupling Reactions. A general Regiospecific Route to Oxygenerated Dibenzo[b,d]pyran-6-ones Related to Ellagic Acid, J. Org. Chem. 1991, 56, 3763-3768.
*** Archer et al; "cannabinoids, synthesis approaches to 9-ketocannabinoids."; J. Org. Chem.; vol. 42; No. 13; 2277-2284; (1977).
Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).
Beak, P.; and Brown, R A., The Tertiary Amide as an Effective Director of Ortho Lithiation, J. Org. Chem. 1982, 47, 34-36.
Belgaonkar et al; "synthesius of isocoumarins"; Indian J. Chem; vol. 13; No. 4; 336-338; 1975 (abstract only).
Berdyshev EV, Cannabinoid receptors and the regulation of immune response. Chem Phys Lipids. Nov. 2000; 108(1-2):169-90.
Bodnar, V.N., Lozinskii, M.O., Pel'kis, P.S.; "Synthesis fo 2,5-disubstitued 1,3,4-oxadiazoles and 1, 4-dihyro-1,2,4,5-tetrazines"; Ukrainskii Khimicheskii Zhurnal (Russian Edition); 48(12); 1308-1311; 1982 (abstract only).
Bracey, M et al, Structural Adaptations in a Membrane Enzyme That Terminates Endocannabinoid Signaling. Science 2002; 298(5599): 1793-1796.
Brennesien R, Pgli A, Eloshly MA, Henn V. Spiess Y: The effect of orally and rectally administered Δ9—tetrahydrocannabinol on spasticity, a pilot study with 2 patients. Int. J. Clin Pharmacol Ther. (1996) 34:446-452. (abstract only).
*** Brotchie JM: *Adjuncts to dopamine replacement a pragmatic approach to reducing the problem of dyskinesia in Parkinson's disease. Mov. Disord.* (1998)13:871-876.
Brown et al; "Synthesis and hydroboration of (-)-20phenylapopinene, Comparison of mono(2-phenylaposiopinocampheyl)borane with its 2-methyl and 2-ethyl analogues for the chiral hydroboration of representative alkenes"; J. Org. Chem.; 55(4); 1217-1223; (1990).
Buckley NE, McCoy KI, Mpzey E et al, "Immunomodulation by cannabinoids is absent in mice deficient for the cannabinoid CB2 receptor"; Eur. J Pharmacol (2000) 396:141-149.
Burstein et al; "detection of cannabinoid receptors . . . "; Biochem. Biophys. Res. Commun.; vol. 176(1); 492-497; 1991 (abstract only).
Busch-Peterson et al; "Unsaturated side chain beta-11-hydroxyhexahydrocannabinol analogs"; J. Med. Chem.; 39; 3790-3796; (1996).
Calignano A, La Rana G. Diuffrida A, Piomelli D; "Control of pain initiation by endogenous cannabinoids"; Nature (1998) 394:277-291. (abstract only).
Cambell FA et al; "Are cannabinoids an effective and safe treatment option in the management of pain? A qualitative systematic review"; BMJ. Jul. 7, 2001;323(7303):13-6.
Charalambous A. et al; "5'-azido Δ8-THC: A Novel Photoaffinity Label for the Cannabinoid Receptor"; J. Med. Chem., 35, 3076-3079 (1992).
Charalambous A. et al; "Pharmacological evaluation of halogenated . . . "; Pharmacol. Biochem. Behav.; vol. 40; No. 3; 509-512; 1991.

Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).

Colombo G, Agabio R, Diaz G. et al; "Appetite suppression and weight loss after the cannabinoid antagonist SR141716"; Life Sci. (1998) 63-PL13-PL117. (abstract only).

Compton et al; "Synthesis and pharmacological evaluation of ether and related analogues of delta8-, delta9- and delta9,11-tetrahydrocannabinol"; J. Med. Chem; vol. 34; No. 11; 3310-3316; 1991.

Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23: 1069-1071; (1970) (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

D'Ambra et al; "C-attached aminoalkylindoles: potent cannabinoid mimetics"; Bioorg. & Med. Chem. Lett., 1996, 6(1), 17-22.

DePetrocellis L, Melck D, Palmisano A. et al; "The endogenous cannabinoid anadamide inhibits human breast cancer cell proliferation"; Proc. Natl. Acad. Sci. USA (Jul. 1998) 95:8375-8380.

Devane, W.A. et al; "Determination and Characterization of a Cannabinoid Receptor in a Rat Brain"; Mol. Pharmacol., 34, 605-613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

*** Dodd, P.R. et al, A Rapid Method for Preparing Synaptosomes: Comparison with Alternative Procedures, Brain Res., 226, 107-118 (1981).

Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylinodles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-Δ9-Tetrahydrocannabinol and Four of Its Isomers"; J. Amer. Chem. Soc. 1967, 89(23), 5934-5941.

Fahrenholtz; "the Synthesis of 2 metabolites of (-)-delta eight-tetrahydrocannabinol"; J. Org. Chem.; vol. 37(13); 1972; XP002111824.

Fisera, L., Kovac, J., Lesco, J., Smahovsky, V.; "Furan derivatives. Part CLVL, 1,3-dipolar cycloadditions of heterocycles. V. Reaction of C-acetyl-N-phenylnitrilimine with furan derivatives"; Chemicke Zvesti; 35(1); 93-104 1981 (abstact only).

Galiegue S et al.; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

Gold et al; "A compariosn of the discriminative stimulus properties of delta9-tetrahydrocannabinol and CP 55,940 in rats and rhesus monkeys"; J. Pharmacol. Exp. Ther.; vol. 262(2); 479-486; 1992.

*** Green K. Marijuana smoking vs. cannabinoids for glaucoma therapy. Arch. Ophibalmol. (Feb. 1998) 433-1437.

Hampson, A.J., Grimaldi M. Axpirod J. Wink D; "Cannabidol and (-) Δ9 tetrahydrocannabinol are neuroprotective antioxidants"; Proc. Natl Acad Sci. USA (Jul. 1998) 95; 8268-8273.

Hargreaves, K. et al; "A new sensitive method for measuring thermal nociception in cutaneous hyperalgesia"; Pain; 32; 77-88; (1988) (abstact only).

*** Hemming M, Yellowlese PM; "Effective treatment of Tourette's syndrome with marijuana"; J. Psychopharmaccol, (1993) 7:389-391.

Herzberg U, Eliav E, Bennett GJ, Kopin IJ; "the Analgesic effects of R(+) WIN 55,212-2 mesylate, a high affinity cannabinoid agonist in a rat model of neuropathic pain"; Neurosci. Letts. (1997) 221; 157-160.

*1* Hillard C. J., Edgemond, W. S., Jarrahian W., Campbell, W. B; "Accumulation of N-Arachibonoylethanolamine (Anandamide) into Cerebellar Granule Cells Occurs via Facilitated Diffusion"; Journal of Neurochemistry; 69; 631-638 (1997).

*1* Horrevoets A.J.G et al; "Inactivation of reconstituted Escherichia coli outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbutl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocannabinols"; tetrahedron; vol. 51(4); 1017-1032; (1995).

Huffman et al; "Synthesis of 5', 11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

*** Joy JE, Wagtson SJ, Benson JA; "Marijuana and Medicine Assessing the Science Base"; National Academy Press, Washington, DC, USA (1999).

Kaminski NE; "Regulation of the cAMP cascade, gene expression and Immune function by cannabinoid receptors"; J Neuroimmunol. Mar. 15, 1998;83(1-2):124-32.

*1* Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

Lavalle et al; "Efficient conversion of (1R, 5R)-(+)-alpha-pinene to (1S, 5R)-(-)-nopinene"; J. Org. Chem.; vol. 51(8); 1362-1365; (1986).

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A compariosn of the synthetic utility of n-butyl-lithium and lithium diisopropylamide in the metalations of N,N-dialkyltouamides"; J. Org. Chem.; 38(9); 1668-1674 (1973).
\*\*\* Maccarron M., Endocannabinoids and their actions. Vitamins and Hormones 2002;65:225-255.
\*\*\* Markwell et al; Anal. Biochem.; 87:206 (1978).
Martin et al; "Behavioral, biochemical, and molecular modeling evaluations of cannabinoid analogs"; Pharmacol. Biochem. Behav.; vol. 40(3); 471-478; 1991.
Martyn CN. Illis LS, Thom J.; "Nabilone in the treatment of multiple sclerosis"; Lancet (1995) vol. 345; pp. 579.
Matsumoto et al; "Cannaabinoids 1.1-amino-and 1 mercapto-7, 8, 9, 10-tetrahydro-6h-dibenzo[b,d]pyrans"; J. of Med. Chem.; vol. 20(1); 17-24; 1977; XP00211825.
\*\*\* Maurer M, Henn V, Dittrich A, Hofmann A. Delta-9-tetrahydrocannabinol shows antispastic and analgesic effects in a single case double-blind trial. Eur. Arch. Psychiat. Clin. Neurosci. (1990), Z40:1-4.
Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.
Mechoulam et al; "Stereochemical Requirements for cannabinoid activity"; J. Med. Chem.; 23(10); 1068-1072; (1980).
Mechoulam et al; "Synthesis of the individual, pharmacologically distinct, enantiomers of a tetrahydrocannabinol derivative"; Tetrahedron Asymmetry; 1: 311-314; (1990) (abstract only).
\*\*\* Mechoulam et al; Tetrahedron Asymmetry; 1: 315-318; (1990).
\*\*\* Mechoulam, "Cannabinoids as therapeutic agents"; CRC press, 1986.
Meltzer et al; "An improved synthesis of cannabinol and cannabiorcol"; Synthesis; 1981:985 (1981).
\*\*\* Melvin et al; drug design and discovery; 13; 155-166 (1995).
Melvin et al; "Structure-activity relationships for cannabinoid receptor-binding and analgesic activity: studies of bicyclic cannabinoid analogs"; Mol Pharmacol.; 44(5): 1008-1015 (1993).
Merck Index; 11th edition; "tetrahydrocannabinols" compound No 9142; 1989.
\*\*\* Morgan Dr: Therapeutic Uses of Cannabis. Harwood Academic Publishers, Amsterdam. (1997).
\*\*\* Morris, S,; Mechoulam, R.; and Irene, Y., Halogenation of phenols and Phenyl ethers with Potassium Halides in the Presence of 18-Crown-6 on Oxidation with m-Chloroperbenzoic Acid, J. Chem. Soc., Perkin Trans. 1 1987, 1423-1427.
\*\*\* Muller-Vahl KB, Kolbe H, Schneider U, Emrich, HM Cannabis in movement disorders. Porsch. Kompicmentarmed (1996) 6 (suppl. 3) 23-27.
\*\*\* Muller-Vahl KB, Schneider U, Kolbe H, Emrich, HM. Treatment of Tourette's syndrome with delta-9-tetrahydrocannaibiol. Am. J. Psychiat. (1999) 156-195.
\*\*\* Nahas G, Marijuana and Medicine; 199, Human Press Inc., Totowa, N.
Novak, J et al; Cannabis, part 27, synthesis of 8-, 10- and 11-oxygeneated cannabinoids; J. Chem. Soc. Perkin Trans.; 2867-2871; (1983) (abstract only).
Nye et al; "High affinity cannabinoid binding sites in brain membranes labelled with [H]-5'-trimethylammonium delta8-tetrahydrocannabinol"; J. Pharmacol. Exp. ther.; vol. 234(3); 784-791; 1985.
\*\*\* Palmer et al; current pharmaceutical design; 6; 1381-1397; (2000).
Papahatjis et al; "A new ring-forming methodology for the synthesis of confromationally constrained bioactive molecuels"; Chemistry Letters, 192; (2001).
Papahatjis et al; "Pharmacophoric requirements for cannabinoid side chains: multiple bond and C1'-substituted delta8-tetrahydrocannabinols"; J. Med. Chem.; 41(7); 1195-1200; (1998).
Pertwee et al; "AM630, a competitive cannabinoid receptor agonist"; Life Sci. 1995,56(23/24), 1949-1955; XP 000653566.
Pertwee et al; "Pharmacological characterization of three novel cannabinoid receptor agonists in the mouse isolated vas deferens"; Eur. J. Pharmacol. 1995, 284, 241-247; XP-001041044.

Pertwee; Pharmacology of cannabinoid CB1 and CB2 receptors; Pharmacol. Ther., vol. 74(2); pp. 129-180; (1997); XP002226467.
Petrov, M.L., Terent'eva, N.A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-PhenyInitrilimine"; Zhurnal Organicheskoi Khimii; 29(7); 1372-1378; (1993) (abstract only).
\*\*\* Pinnegan-Ling D, Musty R.; Marinol and phantom limb pain: a case study. Proc Inv. Cannabinoid Rea. Sec. (1994):53.
Pitt et al; "The synthesis of Deuterium, carbon-14 and carrier free tritium labellled cannabinoids"; Journal of Labellled Compounds; vol. 11(4); 551-575; 1975; XP002123229.
Razdan et al; "Drugs derived from cannabinoids. 6. . Synthesis of cyclic analogues of dimethylheptylpyran"; J. Med. Chem.; vol. 19(5); 719-721; 1976 (abstract only).
Reggio et al; "Characterization of a region of steric interference at the cannabinoid receptor using the active analog approach"; J. Med. Chem. United States; vol. 36(12); 1761-1771; 1993.
Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.
\*\*\* Rice AS. Cannabinoids and pain. Curr Opin Investig Drugs. Mar. 2000;2(3):399-414.
Richardson JD, Aanonsen I, Hargreaves KM; "Antihyperalgesic effects of spinal cannabinoids"; Eur. J. Pharmacol. (1998) 346:145-153.
Richardson JD, Kilo S. Hargreaves KM; "Cannabinoids reduce dryperalgesia and inflammation via interaction with peripheral CB1 receptors"; Pain (1998) 75:111-119.
Rinaldi-Carmona et al; "Biochemical and pharmacological characterization of SR141716A, the first potent and selective brain cannabinoid receptor antagonist"; Life Sci.; vol. 56(23/24); 1941-1947 (1995).
Rinaldi-Carmona et al; "SR141716A, a potent and selective antagonist of the brain cannabinoid receptor"; FEBS Lett.; 350; 240-244; (1994).
Rompp Chemie Lexikon; Falbe and Regitz; "band 1-A-C1, 8"; Aufl, Thieme Verlag; Stuttgart, S 569-570; 1989.
Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).
Schatz AR et al; "Cannabinoid receptors CB1 and CB2: a characterization of expression and adenylate cyclase modulation within the immune system"; Toxicol Appl Pharmacol. Feb. 1997; 142(2):278-87.
\*\*\* Schuel, H., Burkman, L.J., Picone, R.P., Bo, T., Makriyannis, A., Cannabinoid receptors in human sperm. Mol. Biol. Cell., (1997) (8), 325a.
Shawali, A.S., Albar, H.A.; "Kinetics and mechanism of dehydrochlorination of N-aryl-C-ethoxycarbonyl formohydrazidoyl chlorides"; Canadian Journal of Chemistry; 64(5); 871-875; 1986 (abstract only).
\*\*\* Shen M. Thayer SA: Cannabinoid receptor agonists protect cultured rat hippocampal neurons from exitotoxicity. Mol. Pharmacol (1996) 54:459-462.
Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.
Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.
Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.
\*\*\* Simiand J, Keane M, Keane PE, Soubrie P: SR 141716, A CB1 cannabinoid receptor antagonist, selectively reduces sweet food intake in marmoset. Behav. Pharmacol (1998) 9:179-181.

\*\*\* Terranova J-P, Storme J-J Lafon N et al; "Improvement of memory in rodents by the selective CB1 cannabinoid receptor antagonist, SR 141716"; *Psycho-pharmacol* (1996) 126:165-172.

Tius et al; "Conformationally restricted hybrids of CP-55,940 and HHC: Stereoeselective synthesis and activity"; Tetrahedron; 50 (9); 2671-2680; (1994) (abstract only).

\*\*\* Ueda, N., Endocannabinoid hydrolases. Prostaglandins & Other Lipid Mediators 2002;68-69:521-534.

\*\*\* Wagner JA, Varga K, Jarai Z, Kunos G; 'Mesenteric vasodialtion mediated by endothelia anandamide receptors'; Hypertension (1999) 33:429-434.

Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(-)-11-hydroxy-7'-isothiocyanato-1'-1' dimethylheptyl-delta8-THC: a novel probe for the cannabinoid receptor in the brain"; J. Med. Chem.; 37(23); 3867-3870; (1994).

Archer et al; "cannabinoids, synthesis approaches to 9-ketocannabinoids"; J. Org. Chem.; vol. 42; No. 13; 2277-2284; (1977).

\*1\* Lang, W. et al; "Substrate Specificity and Stereoselectivity of Rat Brain Microsomal Anandamide Amidohydrolase"; J. Med. Chem.; vol. 42(5); 869-902; (1999).

\*1\* Sheskin, T. et al; Structural Requirements for Binding of Anandamide Type Compounds to the Brain Cannabinoid Receptor; J. Med. Chem.; 1997; 40: 659-667.

\*1\* Smith P.B. et al; "The pharmacological activity of anandamide, a putative endogenous cannabinoid, in mice"; Journal of Pharmacology and Experimental Therapeutics; vol. 270(1):219-227; 1994.

Beltramo M., Piomelli D; "Anandamide Transport Inhibition by the Vanilloide Agonist Olvanil"; European J. of Pharmacology; (1999); 364(1); 75-78 (abstract only).

\*2\* Brotchie JM: Adjuncts to dopamine replacement a pragmatic approach to reducing the problem of dyskinesia in Parkinson's disease. Mov. Disord. (1998)13:871-876. (abstract only).

\*2\* Compton D.R. et al; "Pharmacological Profile of a Series of Bicyclic Cannabinoid Analogs: Classification as Cannabimimetic Agents"; J. Pharmacol. Exp. Ther.; 260; 201-209; 1992. (abstract only).

Di Marzo, V., Bisogno, T., Melck, D., Ross, R., Brockie, H., Stevenson, L., Pertwee, R., DePetrocellis, L., "Interactions between synthetic vanilloids and the endogenous cannabinoid system"; FEBS Letters; (1998); 437(3); 449-454. (abstract only).

\*2\* Dodd, P.R. et al, A Rapid Method for Preparing Synaptosomes: Comparison with Alternative Procedures, Brain Res., 226, 107-118 (1981) (abstract only).

\*2\* Green K.; "Marijuana smoking vs. cannabinoids for glaucoma therapy."; Arch. Ophthamol. (Nov. 1998) 116(11); 1433-1437. (abstract only).

Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

Hanus et al; "Two new unsaturated fatty acid ethanolamides in brain that bind to the cannabinoid receptor", Journal of medicinal Chemistry; 36(20); 3032-3034; 1993.

Jbilo, O., Derocq, J., Seguri, M., Le Fur, G., Casellas, P.; "Stimulation of peripheral cannabinoid receptor CB2 induces MCP-1 and IL-8 gene expression in human promyelocytic cell line HL60"; FEBS Letters; (1999); vol. 448; No. 21848; 273-277.

\*2\* Joy JE, Wagtson SJ, Benson JA; "Marijuana and Medicine Assessing the Science Base"; National Academy Press, Washington, DC, USA (1999). (abstract only).

Lang, W. et al; "Substrate Specificity and Stereoselectivity of Rat Brain Microsomal Anandamide Amidohydrolase"; J. Med. Chem.; vol. 42(5); 896-902; (1999).

\*2\* Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only).

Mechoulam et al; Structural Requirements for Binding of Anandamide Type Compounds to the Brain Cannabinoid Receptor; J. Med. Chem.; 1997; 40; 659-667.

Mechoulam et al; "Towards Cannabinoid drugs—Revisited"; Progress in Medicinal Chemistry; 35; 199-243; Jul. 3, 1998.

Melck, D., Bisogno, T., DePetrocellis, L., Chuang, H., Julius, D., Bifulco, M., Dimarzo, V.; "Unsaturated Long-Chain N-Acyl-vanillyl-amides"; Biochemical and Biophysical Res. Commun.; (1999); 262(1); 275-284 (abstract only).

Meltzer et al; "An improved synthesis of cannabinol and cannabiorcol"; Synthesis; 1981:985 (1981).

\*2\* Melvin et al; "Structure-Activity Relationships Defining the ACD-Tricyclic Cannabinoids Cannabinoid Receptor Binding and Analgesic Activity"; Drug Design and Discovery; 13(2); 155-166 (1995). (abstract only).

Meschler, J.P., Kraivhely, D. M., Wilken, G. H., Howlett, A. C.; "Inverse Agonist Properties of N-(Piperidin-1-yl)-5-(4-chlorophenyl)-1-(2,4-dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoid Receptor", Biochemical Pharmacology; (2000); vol. 60; No. 9; 1315-1322.

\*2\* Muller-Vahl KB, Kolbe H, Schneider U, Emrich, HM Cannabis in movement disorders. Porsch. Kompicmentarmed (1999) 6 (suppl. 3) 23-27. (abstract only).

\*2\* Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

Pacheco M, et al; "Aminoalkylindoles: Actions on Specific G-Protein-Linked Receptors"; J. Pharmacol. Exp. Ther.; vol. 257, No. 1, pp. 170-183 and 172 Table (1991).

\*2\* Palmer et al; "Natural and Synthetic Endocannabinoids and Their Structure-Activity Relationships"; Current Pharmaceutical Design; 6; 1381-1397; (2000).

\*2\* Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

Pinto et al; Cannabinoid Receptor Binding and Agonist Activity of Amides and Esters of Arachidonic Acid; Mol. Pharmacol.; 1994; 46(3); 516-522.

\*2\* Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

Razdan et al; "Pharmacological and Behavioral Evaluation of Alkylated Anandamide Analogs"; Life Sci.; 1995; 56(23-24); 2041-2048.

\*2\* Rice AS. Cannabinoids and pain. Curr Opin Investig Drugs. Mar. 2001;2(3):399-414. (abstract only).

*2* Serdarevich B., Caroll K.K., "Synthesis and characterization of 1- and 2- monoglycerides of anteiso fatty acids"; J. Lipid Res.; 7; 277-284; (1966).

*2* Shen M. Thayer SA: Cannabinoid receptor agonists protect cultured rat hippocampal neurons from excitotoxiciy. Mol. Pharmacol (1996) 54:459-462.

*2* Simiand J, Keane M, Keane PE, Soubrie P: SR 141716, A CB1 cannabinoid receptor antagonist, selectively reduces sweet food intake in marmoset. Behav. Pharmacol (1998) 9:179-181. (abstract only).

*2* Terranova J-P, Storme J-J Lafon N et al; "Improvement of memory in rodents by the selective CB1 cannabinoid receptor antagonist, SR 141716"; Psycho-pharmacol (1996) 126:165-172 (abstract only).

Tetko, I. V. et al; "Volume Learning Algoritm Artificial Neural Networks For 3D QSAR Studies"; J. Med. Chem.; vol. 44, No. 15 (2001) pp. 2411-2420, 2413, 2414 Table 1.

*2* Ueda, N., Endocannabinoid hydrolases. Prostaglandins & Other Lipid Mediators 2002;68-69:521-534 (abstract only).

*2* Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

*2* Wagner JA, Varga K, Jarai Z, Kunos G; "Mesenteric Vasodilation Mediated by Endothelia Anadamide Receptors"; Hypertension (1999) 33:429-434.

* cited by examiner

RETRO-ANANDAMIDES, HIGH AFFINITY AND STABILITY CANNABINOID RECEPTOR LIGANDS

CROSS-REFERENCE TO RELATED APPLICATIONS

This application is the National Stage of International Application No. PCT/US00/41248, filed Oct. 18, 2000, which claims the benefit of Provisional Application No. 60/160,033, filed on Oct. 18, 1999 and a continuation-in-part of application Ser. No. 09/600,786 filed Jul. 21, 2000 now U.S. Pat. No. 7,161,016 which is the National Stage of International Application No. PCT/US99/28136, filed Nov. 29, 1999, which claims the benefit of Provisional Application No. 60/109,615, filed on Nov. 24, 1998.

FIELD OF THE INVENTION

The present invention relates generally to cannabinoid analogs and is more particularly concerned with new and improved retro-anandamide cannabinoid analogs exhibiting high binding affinities for cannabinoid receptors, pharmaceutical preparations employing these analogs and methods of administering therapeutically effective amounts of the preparations to provide a physiological effect.

BACKGROUND OF THE INVENTION

Classical cannabinoids such as the marijuana derived cannabinoid $\Delta^9$-tetrahydrocannabinol, ($\Delta^9$-THC) produce their pharmacological effects through interaction with specific cannabinoid receptors in the body. So far, two canabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects. See, for example, Pertwee, R. G., *Pharmacology of cannabinoid CB1 and CB2 receptors,* Pharmacol. Ther., (1997) 74:129-180 and Di Marzo, V., Melck, D., Bisogno, T., DePetrocellis, L., *Endocannabinoids: endogenous cannabinoid receptor ligands with neuromodulatory action,* Trends Neurosci. (1998) 21:521-528.

In addition to acting at the cannabinoid receptors, cannabinoids such as $\Delta^9$-THC also affect cellular membranes, thereby producing undesirable side effects such as drowsiness, impairment of monoamine oxidase function and impairment of non-receptor mediated brain function. The additive and psychotropic properties of some cannabinoids also limit their therapeutic value.

Arachidonylethanolamide (anandamide) is an endogenous lipid that binds to and activates the CB1 cannabinoid receptor with approximately equal affinity to that of $\Delta^9$-THC.

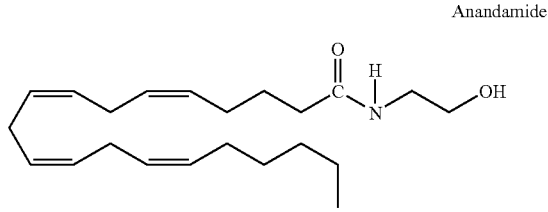

Anandamide

Anandamide also exhibits biochemical and pharmacological properties similar to that of $\Delta^9$-THC, albeit with a longer onset time and shorter duration of action. The exact physiological role of anandamide, a cannabinoid agonist, is still not clearly understood. It is known that an enzyme called "anandamide amidase" hydrolyzes anandamide. It is presumed that the magnitude of action and relatively short duration of action of anandamide is due to a rapid inactivation process consisting of carrier-mediated transport into cells followed by intra-cellular hydrolysis by anandamide amidase.

Presently known anandamide analogues show susceptibility towards enzymatic hydrolysis and/or have low receptor affinity. There is considerable interest in developing analogs of anandamide possessing high CB1 receptor affinity and/or metabolic stability. Such analogs may offer a rational therapeutic approach to a variety of disease states in which elevation of anandamide analog levels may bring about a more favorable response with fewer side effects and greater metabolic stability than direct activation of CB1 receptors by anandamide.

SUMMARY OF THE INVENTION

It has now been found that certain novel analogs of anandamide and physiologically acceptable salts thereof possess improved CB1 receptor affinity and selectivity and/or greater metabolic stability than anadamide. The term "metabolic stability" as used herein refers to the resistance to hydrolysis of the subject anandamide analog by anandamide amidase. Thus, the novel analogues described herein should have a longer duration of action then anandamide.

Thus one aspect of the invention are the analogs of anandamide generally shown in structural formula 1. The novel analogs were prepared by structural modification of anandamide. The modifications were primarily made in the ethanolamido head group and included reversing the positions of the NH and CO groups. Such anandamide analogues wherein the NH and CO group positions are reversed are known as "retro-anandamides".

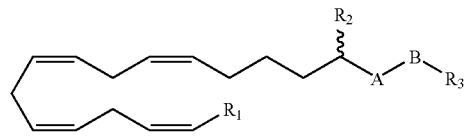

structural formula 1 wherein:

B is selected from C=O and C=S;

A is NH;

$R_1$ is selected from n—$C_5H_{10}D$, n—$C_6H_{12}D$, n—$C_7H_{14}D$, and 1'1'-C($CH_3$)$_2$($CH_2$)$_5CH_2D$, wherein D is selected from H, halogen, $N_3$, NCS, OH, CN and —CH=CH—I;

$R_2$ is selected from H, $CH_3$, and $(CH_3)_2$; and $R_3$ is selected from $CH_3$, $CHE_2$, $CH_2E$, CH=$CH_2$, $CH_2OCH_3$, —C≡CH, —O($CH_2$)n$CH_3$, —S($CH_2$)n$CH_3$, —($CH_2$)n$CH_2E$, ($CH_2$)m$CH_3$—N—($CH_2$)n$CH_3$ wherein E comprises halogen and n and m are each independently a number from 0 to about 7,

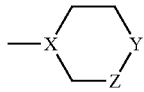

wherein X is selected from N and CH and Y and Z are each independently selected from $(CH_2)_p$, O, N and S, and wherein p is a number from 0 to about 7,

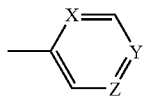

wherein X, Y and Z are each independently selected from CH and N,

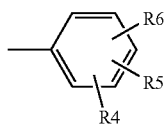

wherein R4, R5 and R6 are each independently selected from hydrogen, halogen, $N_3$, NCS, $OCH_3$, $CH_3$, $CH_2CH_3$, $NO_2$, $NH_2$ and phenyl.

In another aspect of the invention, increased metabolic stability and resistance to enzymatic hydrolysis are achieved by introducing steric bulk in the form of alkyl groups around the amide bond or suitable modification of the amide bond itself.

The inventive anandamide analogues of this invention are metabolically stable (i.e., have low or no enzyme turnover) and show significantly higher cannabinoid receptor affinities and selectivities. The improved receptor affinity and selectivity and/or metabolic stability create therapeutic uses for the novel analogs. Therefore, the novel compounds described herein, and physiologically acceptable salts thereof, represent potentially useful materials for providing a physiological effect to treat The inventive analogs described herein, and physiologically acceptable salts thereof, have high potential when administered in therapeutically effective amounts for providing a physiological effect useful to treat pain; peripheral pain; glaucoma; epilepsy; nausea such as associated with cancer chemotherapy; AIDS Wasting Syndrome; cancer; neurodegenerative diseases including Multiple Sclerosis, Parkinson's Disease, Huntington's Chorea and Alzheimer's Disease; to enhance apetite; to reduce fertility; to prevent or reduce diseases associated with motor function such as Tourette's syndrome; to provide neuroprotection; to produce peripheral vasodilation and to suppress memory. Thus, another aspect of the invention is the administration of a therapeutically effective amount of an inventive compound, or a physiologically acceptable salt thereof, to an individual or animal to provide a physiological effect.

DESCRIPTION OF SOME PREFERRED EMBODIMENTS

As used herein a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Physiological effects which result from cannabinoid receptor stimulation include analgesia, decreased nausea resulting from chemotherapy, sedation and increased appetite. Other physiological functions include relieving intraocular pressure in glaucoma patients and suppression of the immune system. Typically, a "therapeutically effective amount" of the compound ranges from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically to acceptable vehicles may include, for example, saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

The inventive retro-anandamides can generally be described with reference to structural formula 1 and include physiologically acceptable salts thereof.

structural formula 1

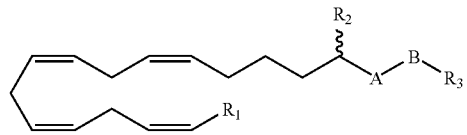

wherein:

B is selected from C=O and C=S;

A is NH;

$R_1$ is selected from n—$C_5H_{10}D$, n—$C_6H_{12}D$, n—$C_7H_{14}D$, and 1'1'-$C(CH_3)_2(CH_2)_5CH_2D$, wherein D is selected from H, halogen, $N_3$, NCS, OH, CN and —CH=CH—I;

$R_2$ is selected from H, $CH_3$ and $(CH_3)_2$; and $R_3$ is selected from $CH_3$, $CHE_2$, $CH_2E$, $CH=CH_2$, $CH_2OCH_3$, —C≡CH, —O$(CH_2)nCH_3$, —S$(CH_2)nCH_3$, —$(CH_2)nCH_2E$ and $(CH_2)mCH_3$—N—$(CH_2)nCH_3$ wherein E comprises halogen and n and m are each independently a number from 0 to about 7,

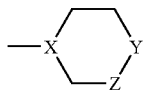

wherein X is selected from N and CH and Y and Z are each independently selected from $(CH_2)_p$, O, N and S, and wherein p is a number from 0 to about 7,

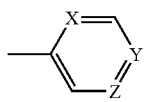

wherein X, Y and Z are each independently selected from CH and N,

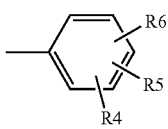

wherein R4, R5 and R6 are each independently selected from hydrogen, halogen, $N_3$, NCS, $OCH_3$, $CH_3$, $CH_2CH_3$, $NO_2$, $NH_2$ and phenyl.

The novel retro-anandamide analogs possess high metabolic stability and/or high CB1 receptor affinity and selectivity. The high CB1 receptor affinity and selectivity functions to make these analogs useful for the treatment of at least the previously described conditions when administered to an individual or animal in a therapeutically effective amount without the unwanted side effects that are a result of use of known cannabinoids to stimulate the CB1 and CB2 receptors. Additionally, the high metabolic stability of the novel analogs function to provide a longer lasting effect than is typical of known cannabinoids.

The inventive materials were generally prepared according to scheme 1 below:

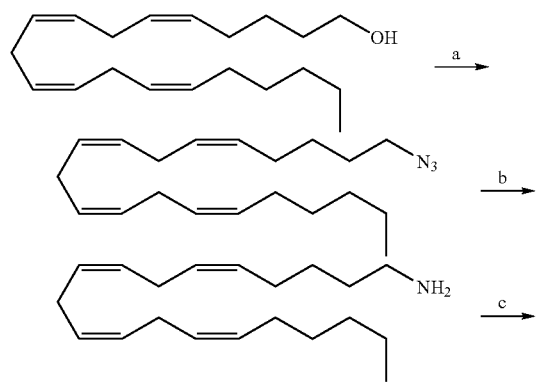

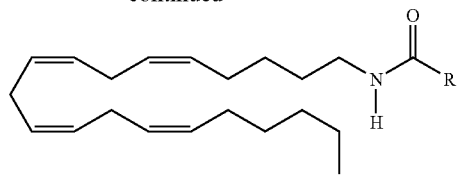

General

Column chromatography was carried out using Selecto Scientific active silica gel (230-400 mesh), and eluents were distilled before use. Solvents for reactions were dried or purified as required. Reactions were carried out under argon atmospheres unless otherwise noted. Arachidonyl alcohol was purchased from Nu-Chek-Prep, Inc., Elysian, Minn. Rat brains were purchased from Pelfreeze Rogers, Ark.

Arachidonyl Azide

To a magnetically stirred solution of 3.6 g (13.7 mmol) of $Ph_3P$ in 30 mL anhydrous toluene was added 2.0 g (6.9 mmol) of arachidonyl alcohol. Then 1.6 g (5.2 mmol) of $ZnN_6 \cdot Py$ was added into the reaction mixture. To this stirred mixture at room temperature, 2.7 mL (13.7 mmol) of diisopropyl azodicarboxylate was added dropwise, causing a slightly exothermal reaction. Stirring was continued until complete consumption (TLC monitoring) of alcohol (<2 hours) was observed. The heterogeneous mixture was filtered over a celite pad, concentrated in vacuo and purified by column chromatography on silica gel with petroleum ether/dichloromethane (5:1) to give 2.0 g (92%) of arachidonyl azide as a colorless oil.

Arachidonyl Amine

To a magnetically stirred solution of 2.0 g (6.3 mmol) of arachidonyl azide in 40 mL of dry diethyl ether was added 10 mL of a 1.0 M solution of lithium aluminum hydride (10 mmol) in THF dropwise at room temperature. The reaction mixture was refluxed for 3 hours (h) and then quenched with wet diethyl ether. The white suspension was filtered, and the filtrate was evaporated to dryness. Chromatography on silica gel (10-50% MeOH in dichloromethane) gave 1.8 g (98%) as a colorless oil.

General Procedure for the Preparation of Retro-anandamides

To a magnetically stirred solution of 0.55 mmol arachidonyl amine and 0.1 mL (0.72 mmol) of triethylamine in 4 mL of anhydrous dichloromethane was added 0.84 mmol of acid chloride in 1 mL dichloromethane. After stirring at room temperature for 3 h, the reaction mixture was added with brine and extracted with dichloromethane. The combined extracts were washed with brine, dried over anhydrous sodium sulfate, filtered, and evaporated. Column chromatography on silica gel with ethyl acetate/petroleum ether gave retro-anandamides as oil.

A person of ordinary skill in the art, understanding the disclosures for the general preparation and specific preparation examples would know how to modify the disclosed procedures to achieve the above listed analogs.

The materials were tested for CB2 receptor binding affinity and for CB1 receptor affinity (to determine selectivity for the CB2 receptor). As used herein, "binding affinity" is represented by the $IC_{50}$ value which is the concentration of an analog required to occupy 50% of the total number (Bmax) of the receptors. The lower the $IC_{50}$ value the higher the binding affinity. As used herein an analog is said to have "binding selectivity" if it has higher binding affinity for one receptor compared to the other receptor; e.g. a cannabinoid analog which has an $IC_{50}$ of 0.1 nM for CB1 and 10 nM for CB2, is 100 times more selective for the CB1 receptor. The binding affinities ($K_i$) are expressed in nanomoles (nM) and are listed in TABLE 1.

It is known that the enzymatic action of anandamide amidase can be moderated or prevented in vitro by the inclusion of phenylmethanesulfonyl fluoride (PMSF). PMSF functions as a non-selective protease inhibitor. Thus the ligand binding determinations for the CB1 receptor were carried out twice, once in the presence and once in the absence of PMSF, to obtain both CB1 receptor binding affinity and a relative measure of the analog's metabolic stability. The binding affinities ($K_i$) are expressed in nanomoles (nM).

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605-613 (1988) and A. Charalambous et al, *5'-azido $\Delta^8$-THC: A Novel Photoaffinity Label for the Cannabinoid Receptor*, J. Med. Chem., 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4 containing 150 μM PMSF (made fresh in 2-propanol as a 100 mM stock). The suspension was incubated at 4° C., and after 15 min a second addition of PMSF stock brought the concentration to 300 μM PMSF; then the mixture was incubated for another 15 min. At the end of the second 15-min incubation, the membranes were pelleted and washed three times with TME to remove unreacted PMSF.

The treated membranes were subsequently used in the binding assay described below. Approximately 30 μg of PMSF-treated membranes were incubated in silanized 96-well microtiter plate with TME containing 0.1% essentially fatty acid-free bovine serum albumin (BSA), 0.8 nM [$^3$H] CP-55,940, and various concentrations of anandamide analogues at 30° C. for 1 hour. The samples were filtered using Packard Filtermate 196 and Whatman GF/C filterplates and washed with wash buffer (TME containing 0.5% BSA). Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099-3102, (1973), which is incorporated by reference herein.

The CB1 ligand binding determinations in the absence of PMSF were performed in a similar manner to the above test, except without the use of PMSF.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981). Silanized centrifuge tubes were used throughout to minimize receptor loss due to adsorption. The CB2 binding assay was conducted in the same manner as for the CB1 binding assay except the assays were conducted without PMSF. Since the CB2 receptor preparation has been shown to be devoid of anandamide amidase, the presence or absence of PMSF was not considered to be determinative. The binding affinities ($K_i$) are expressed in nanomoles (nM).

The following examples are given for purposes of illustration only in order that the present invention may be more fully understood. These examples are not intended to limit in any way the practice of the invention. As used herein, AA refers to that portion of the anandamide molecule having the structure:

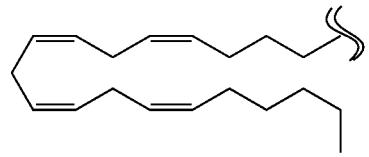

Examples of the following specific analogs were prepared and tested according to the procedures and protocols discussed above.

TABLE 1

| # | Structure | Name |
|---|-----------|------|
| 1 | AA-NH-C(O)-N(morpholine) | N-(4-Morpholinecarbonyl) arachidonylamine |
| 2 | AA-NH-C(O)-CH$_2$CH$_2$-Br | N-(3-Bromopropionyl) arachidonylamine |
| 3 | AA-NH-C(O)-CH$_2$-Cl | N-(2-Chloroacetyl) arachidonylamine |
| 4 | AA-NH-C(O)-CH$_2$-OMe | N-(2-Methoxyacetyl) arachidonylamine |
| 5 | AA-NH-C(O)-CH=CH$_2$ | N-Acryloyl arachidonylamine |
| 6 | AA-NH-C(O)-O-Et | Arachidonylcarbamic acid ethyl ester |
| 7 | AA-NH-C(O)-CHCl$_2$ | N-(2-Dichhloroacetyl) arachidonylamine |

TABLE 1-continued

| | | |
|---|---|---|
| 8 | AA-CH2-NH-C(=O)-CHF2 | N-(2-Difluoroacetyl) arachidonylamine |
| 9 | AA-CH2-NH-C(=O)-N(CH3)-H | N-Dimethylcarbamyl arachidonylamine |
| 10 | AA-CH2-NH-C(=O)-CH3 | N-Acetyl arachidonylamine |
| 11 | AA-CH2-NH-C(=O)-C6H4-F | N-(4-Fluorobenzoyl) arachidonylamine |

TABLE 2

| | $K_i$ (CB1) nM | | |
|---|---|---|---|
| analog | with PMSF | without PMSF | $K_i$ (CB2) nM |
| 1 | 23.9 | 35.4 | 100.3 |
| 2 | 17.4 | 70.6 | very high |
| 3 | 3.33 | 4.39 | 91.4 |
| 4 | 2.08 | 4.22 | 89.8 |
| 5 | 9.06 | 47.8 | 330 |
| 6 | 162.2 | 249.1 | 653.9 |
| 7 | 0.01 | 0.001 | 21.2 |
| 8 | 0.06 | 0.11 | 304.8 |
| 9 | 4.09 | 1.18 | 178.3 |
| 10 | 1.56 | 1.71 | 5320 |
| 11 | 180.7 | 174 | 386 |

Experimental preclinical data using a discriminating behavior test shows at least one of the analogs is 20 to 50 times more potent than the endogenous cannabinoid ligand, anandamide.

The physiological and therapeutic advantages of the inventive materials can be seen with additional reference to the following references, the disclosures of which are hereby incorporated by reference. Arnone M., Maruani J., Chaperon P, et al, *Selective inhibition of sucrose and ethanol intake by SR141716, an antagonist of central cannabinoid (CB1) receptors,* Psychopharmacal, (1997) 132, 104-106. Colombo G, Agabio R, Diaz G. et al: *Appetite suppression and weight loss after the cannabinoid antagonist SR141716.* Life Sci. (1998) 63-PL13-PL117. Simiand J, Keane M, Keane P E, Soubrie P: *SR 141716, A CB1 cannabinoid receptor antagonist, selectively reduces sweet food intake in marmoset.* Behav. Pharmacol (1998) 9:179-181. Brotchie J M: *Adjuncts to dopamine replacement a pragmatic approach to reducing the problem of dyskinesia in Parkinson's disease.* Mov. Disord. (1998) 13:871-876. Terranova J-P, Storme J-J Lafon N et al: *Improvement of memory in rodents by the selective CB1 cannabinoid receptor antagonist,* SR 141716. Psycho-pharmacol (1996) 126:165-172. Hampson A L Grimaldi M. Axpirod J. Wink D: *Cannabidiol and (-) $\Delta^9$ tetrahydrocannabinol are neuroprotective antioxidants.* Proc. Natl Acad Sci. USA (1998) 9S:8268-8273. Buckley N E, McCoy K I, Mpzey E et al *Immunomodulation by cannabinoids is absent in mice deficient for the cannabinoid $CB_2$ receptor.* Eur. J Pharmacol (2000) 396:141-149. Morgan Dr: *Therapeutic Uses of Cannabis.* Harwood Academic Publishers, Amsterdam. (1997). Joy J E, Wagtson S J, Benson J A: *Marijuana and Medicine Assessing the Science Base.* National Academy Press, Washington, D.C., USA (1999). Shen M. Thayer S A: *Cannabinoid receptor agonists protect cultured rat hippocampal neurons from excitotoxicity.* Mol. Pharmacol (1996) 54:459-462. DePetrocellis L, Melck D, Palmisano A. et al: *The endogenous cannabinoid anandamide inhibits human breaast cancer cell proliferation.* Proc Natl. Acad. Sci USA (1998) 95:8375-8380. Green K. *Marijuana smoking vs. cannabinoids for glaucoma therapy.* Arch. Ophibalmol. (1998) feb 433-1437. Hemming M, Yellowlees P M, *Effective treatment of Tourette's syndrome with marijuana.* J. Psychopharmacol, (1993) 7:389-391. Muller-Vahl K B, Schneider U, Kolbe H, Emrich, H M. *Treatment of Tourette's syndrome with delta-9-tetrahydrocannabinol.* Am. J. Psychiat. (1999) 156-195. Muller-Vahl K B, Kolbe H, Schneider U, Emrich, H M *Cannabis in movement disorders.* Porsch. Kompicmentarmed (1999) 6 (suppl. 3) 23-27. Consroe P, Musty R, Rein J, Tillery W, Pertwee R. *The perceived effects of smoked cannabis on patents with multiple sclerosis,* Eur. Neurol. (1997) 38-44-48. Pinnegan-Ling D, Musty R. *Marinol and phantom limb pain: a case study.* Proc Inv. Cannabinoid Rea. Sec. (1994): 53. Brenneisen R, Pgli A, Elsohly M A, Henn V. Spiess Y: *The effect of orally and rectally administered $\Delta^9$-tetrahydrocannabinol on spasticity, a pilot study with 2 patients.* Int. J. Clin Pharmacol Ther. (1996) 34:446-452. Martyn C N. Illis L S, Thorn J. *Nabilone in the treatment of multiple sclerosis.* Lancet (1995) 345:579. Maurer M, Henn V, Dittrich A, Hofmann A. *Delta-9-tetrahydrocannabinol shows antispastic and analgesic effects in a single case double-blind trial.* Eur. Arch. Psychiat. Clin. Neurosci. (1990), Z40:1-4. Herzberg U, Eliav E, Bennett G J, Kopin I J: *The analgesic effects of R(+) WIN 55,212-2 mesylate, a high affinity cannabinoid agonist in a rare model of neuropathic pain.* Neurosci. Letts. (1997) 221:157-160. Richardson J D, Kilo S. Hargreaves K M, *Cannabinoids reduce dryperalgesia and inflammation via interaction with peripheral CB1 receptors.* Pain (1998) 75:111-119. Richardson J D, Aanonsen I, Hargreaves K M: *Antihyperalgesic effects of a spinal cannabinoids.* Eur. J. Pharmacol. (1998) 346:145-153. Calignano A, La Rana G. Diuffrida A, Piomelli D: *Control of pain initiation by endogenous cannabinoids.* Nature (1998) 394: 227-291. Wagner J A, Varga K, Jarai Z, Kunos G: *Mesenteric vasodialtion mediated by endothelia anandamide receptors.* Hypertension (1999) 33:429-434. Schuel, H., Burkman, L. J., Picone, R. P., Bo, T., Makriyannis, A., *Cannabinoid receptors in human sperm.* Mol. Biol. Cell., (1997) (8), 325a.

The inventive analogs described herein, and physiologically acceptable salts thereof, have high potential when administered in therapeutically effective amounts for providing a physiological effect useful to treat pain; peripheral pain; glaucoma; epilepsy; nausea such as associated with cancer chemotherapy; AIDS Wasting Syndrome; cancer; neurodegenerative diseases including Multiple Sclerosis, Parkinson's Disease, Huntington's Chorea and Alzheimer's Disease; to enhance apetite; to reduce fertility; to prevent or reduce diseases associated with motor function such as Tourette's syndrome; to provide neuroprotection; to produce peripheral vasodilation and to suppress memory. Thus, another aspect of the invention is the administration of a therapeutically effective amount of an inventive compound, or a physiologically acceptable salt thereof, to an individual or animal to provide a physiological effect.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:
1. A compound of the formula:

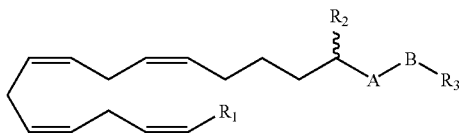

or a physiologically acceptable salt thereof, wherein:
B is selected from C=O, and C=S;
A is NH;
$R_1$ is selected from n—$C_5H_{10}$D, n—$C_6H_{12}$D, n—$C_7H_{14}$D, and 1'1'-C(CH_3)_2(CH_2)_5CH_2D, wherein D is selected from H, halogen, $N_3$, NCS, OH, CN and —CH=CH—I;
$R_2$ is selected from H, $CH_3$, and $(CH_3)_2$; and
$R_3$ is selected from $CHE_2$, $CH_2E$, CH=$CH_2$, $CH_2OCH_3$, —C≡CH, —O($CH_2$)n$CH_3$, —S($CH_2$)n$CH_3$, —($CH_2$)n$CH_2$E and

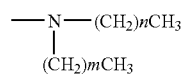

wherein E is halogen and n and m are each independently a number from 0 to about 7,

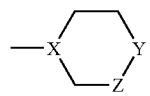

wherein X is selected from N and CH and Y and Z are each independently selected from $(CH_2)_p$, O, N and S, and wherein p is a number from 0 to about 7,

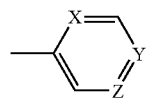

wherein X, Y and Z are each independently selected from CH and N, and

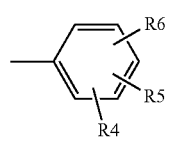

wherein R4, R5 and R6 are each independently selected from hydrogen, halogen, $N_3$, NCS, $OCH_3$, $CH_3$, $CH_2CH_3$, $NO_2$, $NH_2$ and phenyl
with the proviso that, if D is H, $R_2$ is H and B is C=O, then R3 cannot be a phenyl ring, an alkyl phenyl ring or a halogen substituted alkyl phenyl ring.

2. The compound of claim 1 wherein B is C=O.
3. The compound of claim 1 wherein:
B is C=O; and
$R_3$ is selected from $CH_2E$, $CH_2OCH_3$, —C≡CH, —O($CH_2$)n$CH_3$,

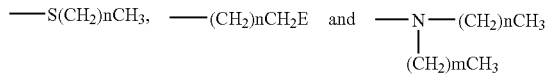

wherein E is halogen and n and m are each independently a number from 0 to about 7,

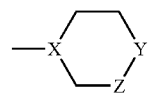

wherein X is selected from N and CH and Y and Z are each independently selected from $(CH_2)_p$, O, N and S, and wherein p is a number from 0 to about 7,

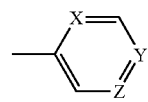

wherein X, Y and Z are each independently selected from CH and N, and

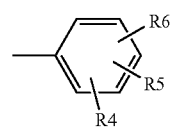

wherein R4, R5 and R6 are each independently selected from hydrogen, halogen, $N_3$, NCS, $OCH_3$, $CH_3$, $CH_2CH_3$, $NO_2$, $NH_2$ and phenyl.

4. A method of binding a compound to cannabinoid receptors in an individual or animal comprising administering to the individual or animal a pharmacological preparation comprising an effective amount of a compound having the formula:

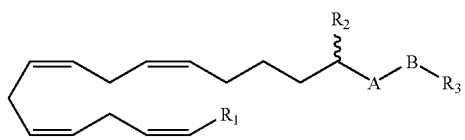

or a physiologically acceptable salt thereof, wherein:
B is selected from C=O, and C=S;
A is NH;

R₁ is selected from n—C₅H₁₀D, n—C₆H₁₂D, n—C₇H₁₄D, and 1'1'-C(CH₃)₂(CH₂)₅CH₂D, wherein D is selected from H, halogen, N₃, NCS, OH, CN and —CH═CH—I;

R₂ is selected from H, CH₃, and (CH₃)₂; and

R₃ is selected from CHE₂, CH₂E, CH═CH₂, CH₂OCH₃, —C≡CH,

—O(CH₂)nCH₃, —S(CH₂)nCH₃, —(CH₂)nCH₂E and

—N—(CH₂)nCH₃
    |
   (CH₂)mCH₃ wherein E is halogen and n and m are each independently a number from 0 to about 7,

[structure: —X / Y / Z ring]

wherein X is selected from N and CH and Y and Z are each independently selected from (CH₂)ₚ, O, N and S, and wherein p is a number from 0 to about 7,

[structure: pyridine-type ring with X, Y, Z]

wherein X, Y and Z are each independently selected from CH and N, and

[structure: phenyl ring with R4, R5, R6]

wherein R4, R5 and R6 are each independently selected from hydrogen, halogen, N₃, NCS, OCH₃, CH₃, CH₂CH₃, NO₂, NH₂ and phenyl with the proviso that if D is H, R₂ is H and B is C═O, then R3 cannot be a phenyl ring, an alkyl phenyl ring or a halogen substituted alkyl phenyl ring.

5. The method of claim 4 wherein:

B is C═O; and

R₃ is selected from CH₂E, CH₂OCH₃, —C≡CH, —)(CH₂)nCH₃,

—S(CH₂)nCH₃, —(CH₂)nCH₂E and —N—(CH₂)nCH₃
                                       |
                                      (CH₂)mCH₃ wherein E is halogen and n and m are each independently a number from 0 to about 7,

[structure: —X / Y / Z ring]

wherein X is selected from N and CH and Y and Z are each independently selected from (CH₂)ₚ, O, N and S, and wherein p is a number from 0 to about 7,

[structure: pyridine-type ring]

wherein X, Y and Z are each independently selected from CH and N, and

[structure: phenyl ring with R4, R5, R6]

wherein R4, R5 and R6 are each independently selected from hydrogen, halogen, N₃, NCS, OCH₃, CH₃, CH₂CH₃, NO₂, NH₂ and phenyl.

6. The compound of claim 1 selected from one of the following structures:

[eight structures showing AA-NH-C(O)- derivatives with various substituents: morpholine urea, CH₂CH₂Br, CH₂Cl, CH₂OMe, vinyl, OEt carbamate, CHCl₂, CHF₂, N(CH₃)₂ urea, 4-F-phenyl]

7. The compound of claim 1 selected from one of the following structures:

[two structures: AA-NH-C(O)-CH₂OMe and AA-NH-C(O)-N(CH₃)₂]

-continued

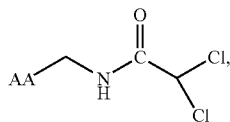 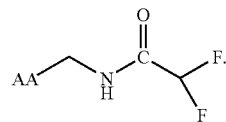

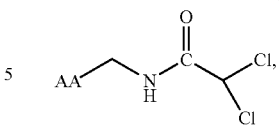 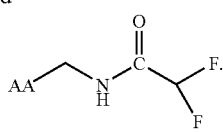

8. The compound of claim 1 having the structure

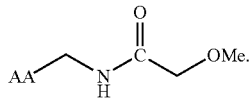

11. The method of claim 4 wherein the compound is

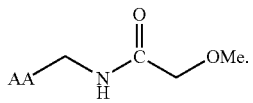

9. The method of claim 4 wherein the compound is selected from one of the following structures:

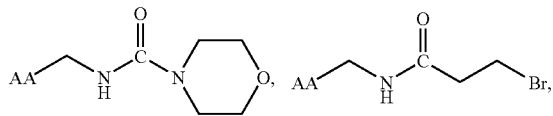

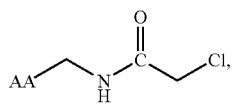

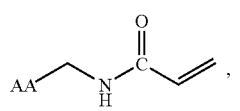

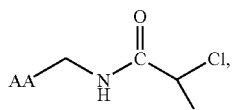

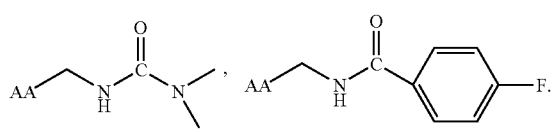

10. The method of claim 4 wherein the compound is selected from one of the following structures:

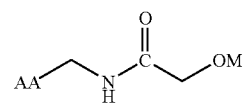

12. The compound of claim 1 wherein $R_3$ is $CH_2OCH_3$.

13. The compound of claim 1 wherein B is C=O; $R_2$ is H; and $R_3$ is $CH_2OCH_3$.

14. The compound of claim 1 wherein B is C=O; $R_2$ is H; $R_1$ is $C_5H_{10}$; D is H; and $R_3$ is $CH_2OCH_3$.

15. The method of claim 4 wherein in the compound $R_3$ is $CH_2OCH_3$.

16. The method of claim 4 wherein in the compound B is C=O; $R_2$ is H; and $R_3$ is $CH_2OCH_3$.

17. The method of claim 4 wherein in the compound B is C=O; $R_2$ is H; $R_1$ is $C_5H_{10}$; D is H; and $R_3$ is $CH_2OCH_3$.

18. A compound of the formula:

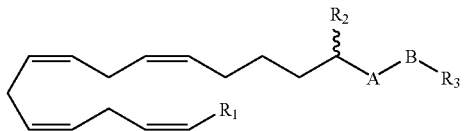

or a physiologically acceptable salt thereof, wherein:
B is C=O;
A is NH;
$R_1$ is selected from n—$C_5H_{10}$D, n—$C_6H_{12}$D, n—$C_7H_{14}$D, and 1'1'-$C(CH_3)_2(CH_2)_5CH_2$D, wherein D is selected from H, halogen, $N_3$, NCS, OH, CN and —CH=CH—I;
$R_2$ is selected from H, $CH_3$, and $(CH_3)_2$; and
$R_3$ is $CH_2OCH_3$.

19. The method of claim 4 wherein the compound selectively binds to CB1 receptors.

20. The method of claim 4 wherein the pharmacological preparation further comprises at least one member selected from an excipient, a vehicle, an adjuvant, a flavoring, a colorant, or a preservative and the compound is in isolated and substantially purified form.

21. The compound of claim 1 wherein the compound is in isolated and substantially purified form.

22. The compound of claim 18 wherein the compound is in isolated and substantially purified form.

* * * * *

UNITED STATES PATENT AND TRADEMARK OFFICE
CERTIFICATE OF CORRECTION

PATENT NO. : 7,276,613 B1  Page 1 of 1
APPLICATION NO. : 10/110862
DATED : October 2, 2007
INVENTOR(S) : Makriyannis et al.

It is certified that error appears in the above-identified patent and that said Letters Patent is hereby corrected as shown below:

On Title Page

Page 1:

Item (63), delete "Nov. 29, 1999" and insert --Nov. 24, 1999--.

Column 13:

Lines 57-58, delete "–) (CH$_2$)nCH$_3$" and insert -- –O(CH$_2$)nCH$_3$--

Column 14:

Line 37, delete

" 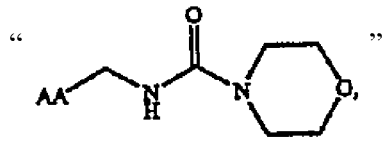 "

And insert

-- 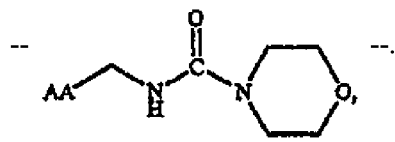 --.

Signed and Sealed this

Eleventh Day of December, 2007

JON W. DUDAS
*Director of the United States Patent and Trademark Office*